United States Patent [19]

Brennen

[11] 3,994,302
[45] Nov. 30, 1976

[54] STIMULATION ELECTRODE OF ION-EXCHANGE MATERIAL

[75] Inventor: Kenneth R. Brennen, Minneapolis, Minn.

[73] Assignee: Medtronic, Inc., Minneapolis, Minn.

[22] Filed: Aug. 14, 1975

[21] Appl. No.: 604,636

[52] U.S. Cl. .............................. 128/404; 128/419 P
[51] Int. Cl.² ............................................. A61N 1/04
[58] Field of Search ............... 128/404, 418, 449 P, 128/410, 411, 417, 2.06 E, 2.1 E, DIG. 4, 172.1

[56] References Cited
UNITED STATES PATENTS

| | | |
|---|---|---|
| 3,416,533 | 12/1968 | Fisher et al. ......................... 128/404 |
| 3,436,329 | 4/1969 | Kahn et al. ......................... 128/2.1 E |
| 3,721,246 | 3/1973 | Landis ................................. 128/418 |
| 3,845,757 | 11/1974 | Weyer ............................ 128/2.06 E |
| 3,911,928 | 10/1975 | Lagergren ............................ 128/418 |

OTHER PUBLICATIONS

Mindt et al., "Stimulating Electrode . . . Consumption", Med. & Biol. Eng., Sept. 1973, pp. 659–660.

Primary Examiner—Robert W. Michell
Assistant Examiner—Lee S. Cohen
Attorney, Agent, or Firm—Schroeder, Siegfried, Ryan & Vidas

[57] ABSTRACT

A stimulating electrode for introducing of electrical signals into animal tissues and in particular into human beings is provided wherein the tissue contacting portion of the electrode is an ion-exchange resin.

16 Claims, 4 Drawing Figures

STIMULATION ELECTRODE OF ION-EXCHANGE MATERIAL

The present invention is directed to the field of stimulation electrodes for application to human tissue to introduce electrical signals into the body. Such electrical signals are utilized for purposes such as muscle stimulation including the heart and for signals such as are used in the blocking of pain.

Heretofore stimulation electrodes of this general type have been formed of inert metal such as platinum and the like. Such electrodes have functioned well and have been used for many years. However, these electrodes of direct metal to tissue contact do possess a number of disadvantages. Many of these disadvantages are overcome through use of the electrode of the present invention.

The electrode of the present invention comprises an ion-exchange material as the electrical signal-transmitting media directly to the human tissue. That is, there is no metallic connection or contact to the human tissue, but rather, a metallic lead terminates in a segment of ion-exchange material which provides the electrical conductivity to the tissue. This type of a system provides the following advantages:

1. It has high internal impedance (in the tens of ohms) which results in less current drain of electrical pulse generators. Particularly where the power source is implanted in the human body, this advantage lessens total power drain from the system improving on its life.

2. The electrode of the invention is less traumatic to the endocardium or other contacting body tissue than metal electrodes as the ion-exchange material can readily be fabricated so as to be both soft and flexible.

3. The risk of cardiac perforation by the electrode is significantly reduced as the electrode does not have sharp or hard surfaces at the point of contact with the tissue.

4. There is no metal to tissue interface. This means that there is decreased electrolysis because of reduced protein contamination of the ion-exchange membrane as compared to metal. Also as the metal is not in contact with the tissue, there is a resultant removal of electrochemical reaction from the point of contact of the electrode-tissue interface to a position within the ion-exchange material itself. That is, there is a change from electronic (metal) conduction to electrolytic conduction within the ion-exchange membrane rather than at the metal tissue interface.

5. There is improved biocompatability over metallic electrodes. At present, the list of metals that have proved to be suitable for the purpose is quite limited. By adaptation of the invention, one can broaden the choice of available materials to a wide variety of ion-exchange resins.

6. One can readily control current distribution by appropriate shaping of the electrodes to the actual tissue involved due to the flexibility and ready shapability of the ion-exchange material over that of metals.

These and other advantages arise from the use of electrodes in accordance with the present invention.

Generally the improved electrode of the present invention comprises an ion-exchange material having a portion of the surface thereof exposed for contact to the tissue region of a patient. The ion-exchange material in turn is in shielded contact with conventional metallic conductors. That is, the metallic lead at its point of junction with the ion-exchange material is suitably shielded by insulation from any possibility of entering into electrochemical reaction with tissue.

By ion-exchange material is meant that class of polymeric materials which contain ionogenic groups which contribute to electrolytic conductance of the bulk material when the material is swollen with water or an electrolyte solution. The charge carriers within the ion-exchange material can be either positive or negative depending on the side groups which have been grafted onto the skeletal structure of the polymeric material to produce the ionogenic characteristics.

The active portion of the electrode in accordance with the present invention utilizes an ion-exchange membrane of the class broadly described above. The choice of materials for such ion-exchange membranes is broad and is subject to restriction only in that it must be formed of a material which is biocompatible. That is, the base polymeric substance and the ionogenic groups must be ones which do not produce adverse reactions with human tissue. Suitable skeleton structures for the base polymer may be formed of materials such as polyethelene, polypropylene, a polystyrenedivinyl benzene copolymer, and phenol formaldehyde.

These are only examples of suitable materials and should not be taken as limiting the number of materials which can be utilized in forming the electrodes in accordance with the invention. To the polymer skeleton or back-bone structure as given above is attached, such as by radiation grafting and/or chemical grafting, ionogenic groups which may include (but are not limited to) sulfonic acid, phosphonic acid, quaternary ammonium groups, polyamines, and carboxylic acid groups. As has already been pointed out the ionogenic groups may be either a positive or negative charge-carrier type. Desirably, the ionic members which will form the charge-carriers should be ions which are commonly found within the tissue. For example, sodium ions and chloride ions are normally available within the animal or human tissue. Therefore, the ion conducting charge carriers within the ion-exchange material can advantageously be formed of sodium ions or chloride ions. This does not mean that other materials cannot be used which will ultimately result in an equilibrium condition, with the materials of the human body. By selection of materials such as sodium or chloride as the ion-charge carrier more rapid equilibration with the human tissue is achieved.

As more specific illustrations of suitable materials one may utilize commercially available resins. One such resin is available from RAI Research Corporation of Hauppauge, Long Island, New York, under their designation JL 1011-80H membrane. This material is a vinyl pyridine grafted to a polyethylene base. As further examples of an ion-exchange membrane usable in the construction of electrodes in accordance with the invention and also available from this same manufacturer, one may utilize P 4025H which is a quaternized vinyl pyridine grafted to fluorinated ethylene propylene. A resin designated P 5010 which is styrene sulfonic acid grafted to a fluorinated ethylene propylene base is yet another suitable material. Innumerable other IEM (ion-exchange materials) may be utilized provided they meet the characteristics set forth above.

Figure 1:
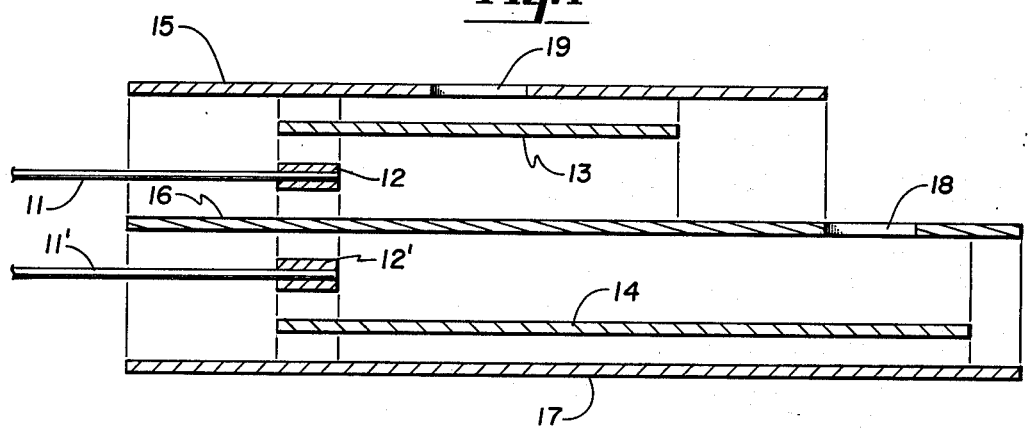
FIG. 1 is a side elevational and cross-sectional exploded view of a bipolar electrode in accordance with the invention prior to completion of assembly.
Figure 2:
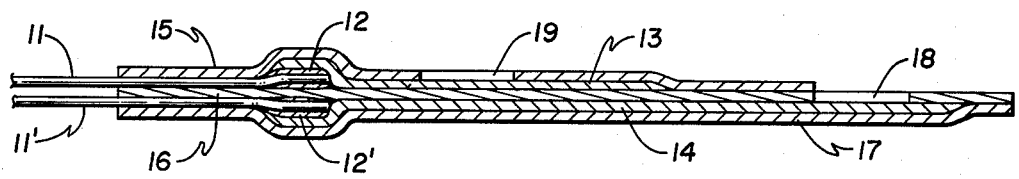
FIG. 2 is the electrode of FIG. 1 after completion of assembly.
Figure 3:
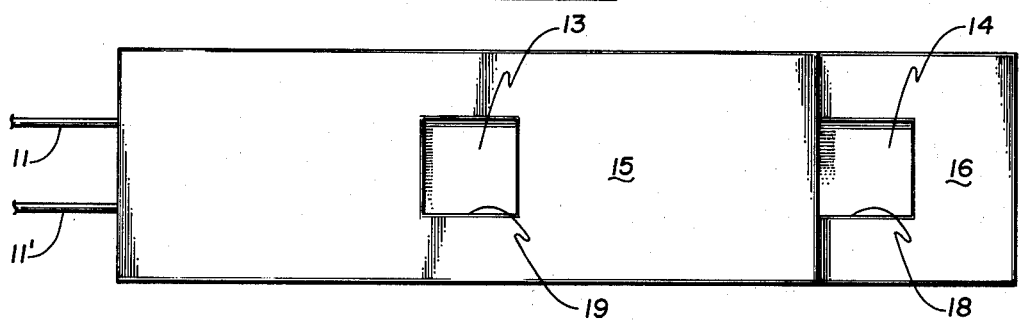
FIG. 3 is a top elevational view of the completed electrodes of FIGS. 1 and 2; and, FIG. 4 is a perspective view of another form of electrode (a unipolar electrode) in accordance with the present invention prior to completion of assembly.

Turning now to the drawings, there is illustrated in FIGS. 1, 2, and 3 an electrode structure in accordance with the present invention. In each of the several views, like parts will be given the same numerical designation. A metallic lead material which may be any of a wide variety of conventional metals such as copper, nickel, or one of the noble metals is generally designated 11. Not shown, but as an essential portion of the electrode construction of the present invention, is the insulating material which would encase all but the active tip portion of the leads 11. This insulation can be any of the conventional biocompatible insulators utilized for leads which are to be used in the human body such as silicone rubbers and the like. The lead insulator will cover lead 11 except for the exposed end that is in electrical communication with the ion-exchange membrane. The metal contact portion of the lead 11 is coated with a mixture of silver-silver chloride at the outermost extremity thereof and is generally designated 12. Layer 12 surrounds the tip of the lead 11 and forms the media for providing electrolytic contact to the membrane material which in turn makes the electrical contact to the body tissue. The membrane material 13 and 14 may be any of the ion-exchange materials which have been previously described both specifically and generally above. In this particular instance, they are of a sheet-like construction.

Facing membranes 13 and 14 and also encompassing the tip ends of lead 11 including the silver chloride material 12 are sheets of insulating plastic material 15, 16 and 17. These materials may conveniently be heat sealable plastics and for the purposes of the present illustration, are polyethylene sheet material. Alternatively, layers 15, 16, and 17 may be joined by use of adhesives. Layer 17 forms the base of the electrode and is within any openings therethrough. Membrane 14 is placed in physical contact therewith and then the lead 11' with its electrode tip 12' is placed into physical contact with membrane 14. Over this particular assembly is placed a spacer and insulating material 16 having a window opening 18 cut therethrough. The window area 18 provides a contact region for membrane 14 to the body tissue. On top of insulating layer 16 is placed electrode assembly 11 and its tip 12 and over this assembly in turn is placed membrane 13. A further insulating film 15 is deposited on the top of the overall assembly. Insulating material 15 has a window region 19 which provides an opening for body tissue contact to ion-exchange material 13. The entire assembly is then sealed as by heat sealing around the peripheral region thereof. This heat sealing further encapsulates the lead members 11 and 11'. As can be seen, regions defined by openings 18 and 19 expose electrodes 13 and 14 of the ion-exchange material for contact to the human tissue.

Figure 4:
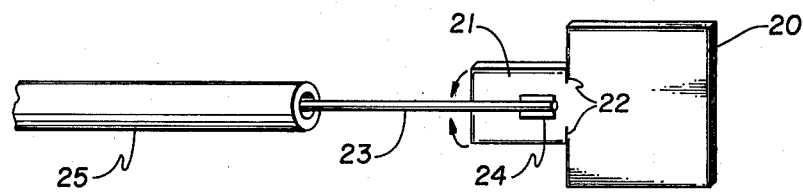

An alternate form of the invention is illustrated in FIG. 4 where an ion-exchange material 20 is of a generally rectangular configuration having a tail portion 21 which is cut at 22 so as to permit wrapping of portions thereof around the lead 23. Lead 23 has a region 24 of the suitable material such as the silver/silver chloride coating the end thereof to provide electrical contact with membrane material 20. After tail portion 21 has been wrapped around and bonded to the lead assembly 23–24, the assembly is then pulled into an insulating sleeve 25 of a material such as silicone rubber that has been expanded by treatment with suitable solvent. Once the lead assembly including the wrap around portion 21 has been pulled into the opening in tubing 25, the solvent is allowed to evaporate to thereby shrink tubing 25 into a tight liquid impermeable juncture about material 2. This leaves exposed the tip membrane electrode 20.

Numerous other constructions will readily occur to those skilled in the art of forming electrodes for contact to the human body. The variety of shaping and assemblies are numerous and will not be described with any further detail herein. It suffices to say that the invention can be readily adapted to a wide variety of electrode configurations so as to meet specific needs for contact to various body tissue regions.

Once such an electrode is formed it is readily placed into contact with the desired portion of the human tissue. If the ion-exchange material has not previously been treated so as to swell same such as by immersion in water or other electrolyte solutions, it can be so treated immediately prior to application to the human tissue. One may even rely upon such swelling resulting from contact with the actual body tissue and fluids after placement thereon. The ion-exchange material will rapidly equilibrate with the body fluids so as to provide the typical body ions into the ionic exchange material. As previously indicated, this will typically be sodium and/or chloride ions. Conduction then occurs between the body tissue and the ion-exchange membrane in such a manner that the advantage heretofore set forth above are achieved.

I claim:
1. The method of establishing a non-metal electrical contact with living tissue comprising:
   a. forming an electrical contact between a metal lead member and an ion-exchange material formed of a body-tissue-compatible polymeric plastic having grafted thereon ionogenic groups;
   b. providing an electrical and fluid seal over said metal lead member and the juncture of said lead member and said ion-exchange material; and,
   c. placing said ion-exchange material in physical contact with living tissue.

2. The method in accordance with claim 1 wherein said ion-exchange material has been swollen prior to application to the living tissue by immersion in an aqueous electrolyte.

3. The method in accordance with claim 2 wherein said aqueous electrolyte is sodium chloride dissolved in water.

4. A non-metallic biomedical electrode for application to living tissue for transmission of electrical signals into the body comprising:
   a. a thin, soft, flexible ion-exchange material formed of a polymer with ionogenic groups grafted to the skeletal structure of the polymer to have ionogenic groups at the exterior surface of the polymer;
   b. a metal lead joined to a portion of said ion-exchange material in electrical contact; and,
   c. an electrically insulating and liquid tight seal over said lead and lead ion-exchange material junction.

5. An electrode in accordance with claim 4 wherein said ion-exchange material is a polymer selected from the group consisting of polyethylene, polypropylene, and polystyrene - divinyl benzene copolymer, fluorinated ethylene propylene, and phenol-formaldehyde and said ionogenic groups grated thereon are selected from the group consisting of sulfonic acid, phosphinic acid, quaternary ammonium, polyamines, carboxylic acid and quaternized vinyl pyridine.

6. An electrode in accordance with claim 5 wherein said ion-exchange material is fluorinated ethylene propylene with sulfonic acid groups grafted thereon.

7. An electrode in accordance with claim 5 wherein said ion-exchange material is polyethylene with sulfonic acid groups grafted thereon.

8. An electrode in accordance with claim 5 wherein said ion-exchange material is polypropylene with sulfonic acid groups grafted thereon.

9. An electrode in accordance with claim 4 wherein said ion-exchange material is vinyl pyridine grafted to a polyethylene base.

10. An electrode in accordance with claim 4 wherein said metal lead has a layer of metal-metal salt on the surface thereof that is in physical contact with said ion-exchange material.

11. An electrode in accordance with claim 10 wherein said metal-metal salt layer is silver-silver chloride.

12. A non-metallic biomedical electrode for application to living tissue for transmission of electrical signals into the body comprising:
   a. first and second thin sheets of an ion-exchange material formed of a polymer with ionogenic groups grafted thereto so that the ionogenic groups are at the exterior surface thereof, each of said sheets having an inner and outer side, said second sheet having a greater length than said first sheet, said first and second sheets being generally in parallel and spaced relationship to one another;
   b. first and second metal lead members joined respectively to a portion of said first and second sheets of ion-exchange material to be in electrical contact therewith;
   c. first, second and third films of insulating plastic, said first film being of greater width and length than said first sheet and shorter than said second sheet and said second and third films having a length and width greater than said first and second sheets;
   d. said sheets and said films being arranged in a multiple layer electrode structure with said first and second sheets having their inner sides facing toward one another and being spaced from one another by said second film with said first sheet being positioned within the perimeter of said second film and said first and third films being positioned on the outer sides with the perimeters extending beyond said first and second sheets respectively, the edges of said first, second and third films that extend beyond said first and second sheets being sealed to one another so as to isolate said first sheet from said second sheet and to have said first and second lead members extending outwardly from and beyond the edges of said films; and,
   e. at least two of said films defining openings respectively therethrough to expose respectively a portion of said first and second sheets to the environment to thereby permit contact of a portion of said first and second sheets to a living tissue.

13. An electrode in accordance with claim 12 wherein said openings are in said first and second films so that said openings expose said first and second sheets on the same side of the electrode structure.

14. An electrode in accordance with claim 12 wherein said ion-exchange material is a polymer selected from the group consisting of polyethylene, polypropylene, and polystyrene-divinyl benzene copolymer, fluorinated ethylene propylene, and phenol-formaldehyde and said ionogenic groups grafted thereon are selected from the group consisting of sulfonic acid, phosphinic acid, quaternary ammonium, polyamines, carboxylic acid and quaternized vinyl pyridine.

15. An electrode in accordance with claim 12 wherein said first and second sheets of ion-exchange material are fluorinated ethylene propylene with sulfonic acid groups grafted thereon.

16. An electrode in accordance with claim 12 wherein said ion-exchange material is polyethylene with sulfonic acid groups grafted thereon.

* * * * *